(12) United States Patent
Grayson

(10) Patent No.: US 6,210,376 B1
(45) Date of Patent: Apr. 3, 2001

(54) CANNULATED DELIVERY PIN

(75) Inventor: Barry H. Grayson, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/288,405

(22) Filed: Apr. 8, 1999

(51) Int. Cl.$^7$ .................................................. A61B 17/00
(52) U.S. Cl. ................................ 604/264; 606/72; 606/73
(58) Field of Search ............................... 606/62, 65, 72, 606/73; 604/264, 523, 174, 175, 272–274

(56) References Cited

U.S. PATENT DOCUMENTS

| | | | |
|---|---|---|---|
| 3,821,956 | 7/1974 | Gordhamer | 128/343 |
| 4,175,555 | 11/1979 | Herbert | 128/92 |
| 4,236,520 | 12/1980 | Anderson | 128/348 |
| 4,573,448 | 3/1986 | Kambin | 128/1 R |
| 4,653,489 | 3/1987 | Tronzo | 128/92 YV |
| 4,670,008 | 6/1987 | Von Albertini | 604/165 |
| 4,769,005 | 9/1988 | Ginsburg et al. | 604/53 |
| 4,784,638 | * 11/1988 | Ghajar et al. | 604/49 |
| 4,950,270 | 8/1990 | Bowman et al. | 606/72 |
| 4,968,306 | 11/1990 | Huss et al. | 604/264 |
| 5,047,030 | 9/1991 | Draenert | 606/65 |
| 5,098,435 | 3/1992 | Stednitz et al. | 606/73 |
| 5,201,723 | 4/1993 | Quinn | 604/264 |
| 5,259,398 | 11/1993 | Vrespa | 128/898 |
| 5,334,204 | 8/1994 | Clewett et al. | 606/73 |
| 5,431,665 | 7/1995 | Li | 606/131 |
| 5,484,442 | 1/1996 | Melker et al. | 606/79 |
| 5,536,127 | 7/1996 | Pennig | 411/413 |
| 5,562,672 | 10/1996 | Huebner et al. | 606/73 |
| 5,601,559 | 2/1997 | Melker et al. | 606/79 |
| 5,662,673 | 9/1997 | Kieturakis | 606/185 |
| 5,718,706 | 2/1998 | Roger | 606/73 |
| 5,725,581 | 3/1998 | Brånemark | 623/16 |
| 5,730,744 | 3/1998 | Justin et al. | 606/73 |
| 5,735,898 | 4/1998 | Brånemark | 623/16 |
| 5,743,912 | 4/1998 | Lahille et al. | 606/65 |
| 5,746,720 | 5/1998 | Stouder, Jr. | 604/117 |
| 5,797,914 | 8/1998 | Leibinger | 606/73 |
| 5,820,604 | 10/1998 | Fox et al. | 604/256 |
| 5,842,865 | 12/1998 | Bassett et al. | 433/174 |

* cited by examiner

Primary Examiner—John B. Yasko
(74) Attorney, Agent, or Firm—Browdy and Neimark

(57) ABSTRACT

A cannulated delivery pin for administering fluids to the bone of a patient, comprising a shaft having a connection end and a pointed end and delivery holes in communication with a central conduit. The delivery holes are angled in a direction away from the pointed end to avoid clogging. Another aspect is a delivery pin having a threaded portion of the shaft adjacent the pointed end and a perforated portion of the shaft adjacent the threaded portion. A delivery system includes the delivery pin as a fixation device. Another aspect is a method for using the delivery pin.

15 Claims, 3 Drawing Sheets

CANNULATED DELIVERY PIN

FIELD OF THE INVENTION

The present invention relates to devices for delivering medication and other fluids through a patient's bone, and in particular to a delivery pin for introducing fluids into bone.

BACKGROUND OF THE INVENTION

There are a number of surgical procedures which involve the delivery of medication and other fluids into the bone of a patient. One example is intraosseous infusion, a procedure for administering fluids into a patient's bloodstream through the medullary cavity of a patient's bones, typically the long bones, jaw bone or pelvis. This procedure allows the medication or other fluids to enter the bloodstream from the medullary cavity within seconds without requiring access to a suitable blood vessel of the patient. In other applications, medication or other fluids are delivered to the cortical plate of patients' bones.

A type of device which is used to deliver fluids into bone is a delivery pin or needle. A delivery needle is used in intraosseous infusion for accessing the medullary cavity of the bone. The needle has a passageway and a number of orifices in communication with the passageway for delivering the fluids into the bone. For boring through bone, the needle has a pointed end and a number of threads spaced longitudinally along the needle. The pointed end may include a self-cutting tip for tapping into and boring into bone. A drill may be used to drill a hole in the bone prior to inserting the needle, if no self-cutting tip is provided. The needle is inserted by rotating the needle with either a drill operated at a low speed, or manually. The needle is inserted until the orifices are appropriately positioned within the patient's bone.

The orifices of delivery pins have a tendency to become clogged with tissue during the advancement of the needle through the bone. U.S. Pat. No. 5,601,559 to Melker et al., the disclosure of which is hereby incorporated by reference herein, discloses orifices which are sized and positioned with respect to threads on the needle to avoid such clogging. Clogging of the orifices of the pin prevents the administration of fluids and may present a possibly life-threatening situation for a patient in dire need of the administration of such fluids.

Threaded pins are also used as fixation devices anchoring other devices to bone. For example, one device for anchoring prostheses in bone includes cutting edges for boring into bone, as well as orifices for providing space into which bone tissue can grow. Such a device is disclosed by Brånemark, U.S. Pat. No. 5,725,581, the disclosure of which is hereby incorporated by reference herein. In these devices as well, bone tissue tends to clog the orifices as the pin advances through the bone. Thus, improvements in needles or pins for delivering medication and other fluids to the bone of a patient are desirable.

SUMMARY OF THE INVENTION

A delivery pin for administering fluids to the bone of a patient comprises a shaft having a connection end and a pointed end. The shaft defines a conduit for communication of fluids and a plurality of delivery holes in communication with the conduit. At least a portion of the delivery holes has a central axis tilted in a direction toward the connection end of the shaft. In preferred embodiments, the pin includes threaded portions for boring through bone. The pin, for example, may include at least a first threaded portion of the shaft which includes threads for boring through bone. The threads are longitudinally spaced along the threaded portion of the shaft. In certain embodiments, at least a portion of the delivery holes are disposed between the spaced threads and distributed on the threaded portion. In other embodiments, the shaft includes a perforated portion disposed in an unthreaded portion of the shaft and the delivery holes are disposed in the perforated unthreaded portion.

The tilted delivery holes of the delivery pin substantially discourages clogging of the delivery pin. The delivery pin may be used in procedures infusing fluids into the medullary cavity or cortical plates of bones and the delivery holes are preferably positioned accordingly. The delivery pin may be also used as a fixation device to fix another device to bone while delivering fluids to the bone.

In certain preferred embodiments, the threaded and perforated portions are positioned along the shaft so that the pin may be positioned as desired. For example, the delivery holes may be spaced from the pointed end so that a threaded portion adjacent the pointed end engages the cortical plate of the bone and the delivery holes are disposed within the medullary cavity. In certain preferred embodiments, the first threaded portion comprises a portion of the shaft adjacent the pointed end of the shaft. The threaded portion may, for example, extend from the pointed end of the shaft to a first intermediate point on the shaft comprising a second end of the first threaded portion. Thus, the pin may include an unthreaded portion adjacent the pointed end and a portion extending from the connection end to the first intermediate point which does not include threads. In certain embodiments, the perforated portion may comprise the unthreaded portion extending from the connection end to the first threaded portion. In other embodiments, the pin includes a second threaded portion adjacent the connection end of the shaft. The second threaded portion extends from the connection end to a second intermediate point so that the perforated portion extends from the second intermediate point to the first intermediate point, between the first and second threaded portions.

In preferred embodiments, the delivery pin further comprises curved segments between the threads. The curved segments may include, for example, surfaces facing the connection end and surfaces facing the pointed end. The delivery holes are desirably defined by the surfaces facing the connection end.

Preferred embodiments also include a trocar for slidable engagement with the conduit of the pin to block the conduit. Preferably, the trocar substantially fills the conduit and prevents the ingrowth of bone. Additionally, the trocar leaves little stagnant area within the conduit for bacterial infection to develop.

Another aspect of the invention provides a delivery pin for administering fluids to the bone of a patient, comprising a shaft having a connection end and pointed end and defining a conduit for the communication of fluids, the shaft including a first threaded portion and an unthreaded portion. The first threaded portion is a portion of the shaft adjacent the pointed end, including threads longitudinally spaced along the first threaded portion for boring through bone and the shaft defines a plurality of delivery holes in communication with the conduit. In preferred embodiments, the delivery pin further comprises a second threaded portion adjacent the connection end and the delivery holes are disposed in the unthreaded portion. At least a portion of the plurality of delivery holes has a central axis tilted in a direction toward the connection end of the delivery pin in preferred embodiments, as discussed above.

Another aspect of the invention is a method of installing the delivery pin to administer fluids to the medullary cavity of a patient's bone by providing a cut in the cortical bone surrounding the medullary cavity and turning the delivery pin so that the threads bore through the cortical bone until the first and second threaded portions are disposed within the cortical bone and the delivery holes are disposed within the medullary cavity of the bone.

BRIEF DESCRIPTION OF THE DRAWINGS

These and other features, aspect, and advantages of the present invention will become better understood with regard to the following description, appended claims and accompanying drawings where:

DETAILED DESCRIPTION OF THE PREFERRED EMBODIMENTS

Figure 3:
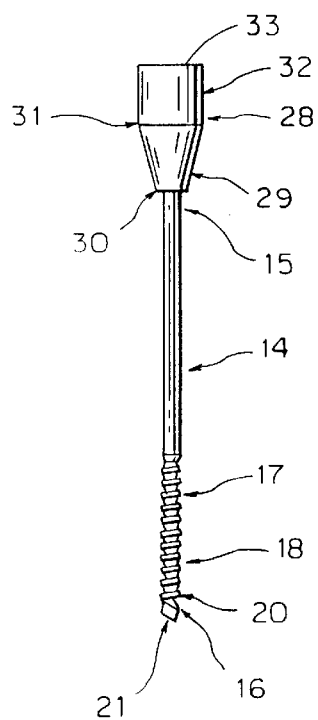
FIG. 3 is a front elevational view of the cannulated pin of FIG. 1.
Figure 4:
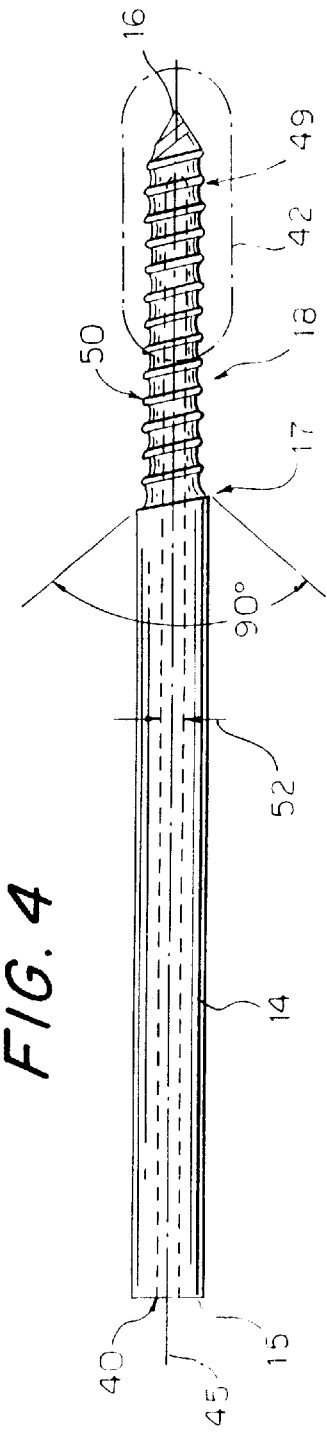
FIG. 4 is a front elevational view of the shaft of the cannulated pin of FIGS. 1–3.
Figure 5:
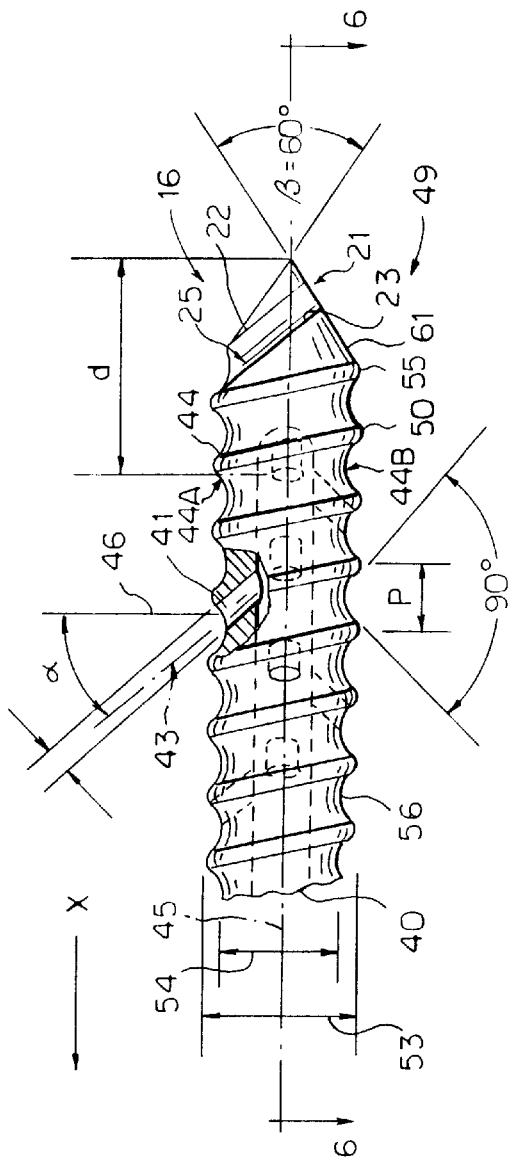
FIG. 5 is a detail of the pointed end of the cannulated pin of FIGS. 1–4.
Figure 6:
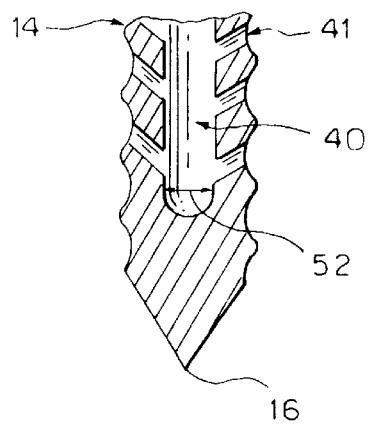
FIG. 6 is sectional view taken along line 6—6 in FIG. 5.

The delivery pin in accordance with an embodiment of the invention depicted in FIGS. 1 through 6 forms a part of a delivery device 12 having a cannulated pin 10 comprising a shaft 14 having a connection end 15 and a pointed end 16. The pointed end 16 of the cannulated pin 10 has an angled side 61 forming an angle β of 60°. A threaded portion 18 of the shaft 14 extends from the pointed end 16 to an intermediate point 17 between the connection end 15 and the pointed end 16. The threaded portion includes threads 50 extending from the pointed end 16 to the intermediate point 17. The threads, as best seen in FIG. 5, are spaced longitudinally along threaded portion 18 of the shaft 14. The spacing between threads 50 is the pitch "P" of the threads. Extending between each thread is a curved segment 44 having a surface 44A facing in the direction of the connection end 15 and another surface 44B facing in the direction of the pointed end 16. The threads include peaks 55, at points furthest from the conduit 40, and valleys 56 closest to the conduit 40 of the embodiment shown.

A notch 21 is provided on the pointed end 16. The notch, as best seen in FIG. 5, includes a first angled edge 22 and a second angled edge 23 and a cutting face 25 extending between the first angled edge 22 and a second angled edge 23. The notch 21 and threads 50 are provided to bore through bone so that the cannulated pin may be inserted into the bone of a patient. Thus, separate drilling of a hole in the patient's bone is avoided as the cannulated pin is "selftapping".

As seen in FIG. 3, the connection end 15 of the shaft 14 is attached to a connector 28 so that the delivery pin may be connected to other devices, as a source of fluids to be delivered by the pin. The connector 28 includes a conical section 29 having a narrow end 30 and a broad end 31. The narrow end is connected to the connection end 15 of the shaft 14. The broad end 31 of the connector 28 is adjacent a broad piece 32 of the connector. At the end of the broad piece 32 opposite the broad end 31, the connector 28 forms an enlarged opening 33. The broad piece 32 of the connector 28 includes an orifice 34 for connection to other devices.

The shaft 14, as best seen in FIG. 4, includes a conduit 40 extending from the connection end 15 to the pointed end 16 of the shaft 14. The shaft 14 has a longitudinal axis 45 about which with the conduit 40 is concentric. A transverse axis 46 is perpendicular to the longitudinal axis 45.

The conduit is in communication with a plurality of delivery holes 41 provided for administering fluids to the bone of the patient. In the particular embodiment shown in FIG. 5, eight holes are spaced along the threaded portion 18 to define a perforated portion 42 of the shaft. The location of the perforated portion is desirably selected according to the procedure in which the delivery pin is used. The delivery holes are placed to be aligned with the part of the bone, such as the cortical plates or medullary cavity, to receive the fluids delivered.

Each delivery hole 41 extends from the conduit 40 to an exterior side 49 of the cannulated pin. The delivery holes are preferably circular in cross section and have a central axis 43, normal to the cross section of the hole. The central axis 43 is angled in a direction X toward the connection end 15 of the shaft 14, forming an angle α with transverse axis 46. Thus, the end of the delivery holes 41 on the exterior side 49 of the cannulated pin 10 are defined by the surface of the curved segment 44A which faces in the direction X, toward the connection end 15. As the cannulated pin 10 is driven through bone, bone fragments are much less likely to enter the delivery holes 41 because the delivery holes are angled away from the pointed end 16. A cannulated pin in accordance with an embodiment of the invention substantially discourages clogging of the delivery holes and provides a more reliable device for administering fluids to a patient.

The conduit is preferably as wide as possible without compromising the structural integrity of the cannulated pin. In addition, the delivery holes should be as wide as possible without capturing fragments of bone. In the particular embodiment shown in FIGS. 1 through 6, the shaft has a length of 1.77" and the threaded portion has a length of 0.596". The shaft has a diameter 51 of 0.093" and the conduit 40 has a conduit diameter 52 of approximately 0.03". The threaded portion 18 of the shaft has a major diameter 53 of 0.079", extending between the peaks 55 of the threads. A minor diameter 54 of 0.059" extends between extending between the valleys 56 of the threads 50 of 0.059". The delivery holes have a hole diameter of 0.015". The pitch P of the threads is 0.039". In the embodiment illustrated, the delivery hole 41 closest to the pointed end 16 is spaced a distance d therefrom of 0.128".

Figure 3A:
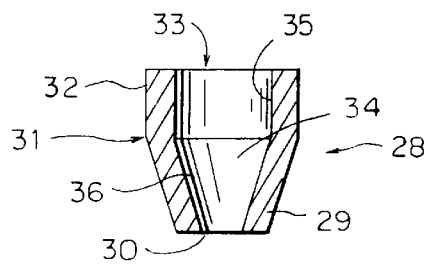
FIG. 3A is a cross-sectional view of the connector of the cannulated pin of FIG. 1.

As illustrated in FIG. 3A, the connector 28 defines a passageway 34 extending from the conduit 40 to the enlarged opening 33. The passageway 34 is defined by an inside wall 35 of the connector 28. In certain preferred embodiments, the wall 35 includes an angled wall 36 of the conical section 29 of the connector 28. The angled wall 36 provides frictional engagement with a source of fluids, such as certain standard intravenous ("I.V.") tubes. Other preferred embodiments of the cannulated pin include threads adjacent the opening 33 of the connector 28 so that the connector will dock with another type of standard I.V. tube.

Figure 1:
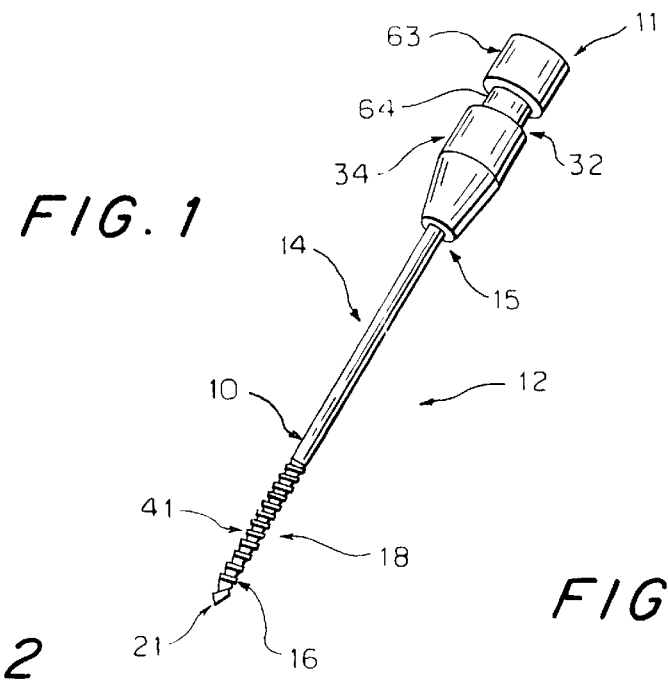
FIG. 1 is a front elevational view of the cannulated pin and trocar in accordance with one embodiment of the invention.
Figure 2:
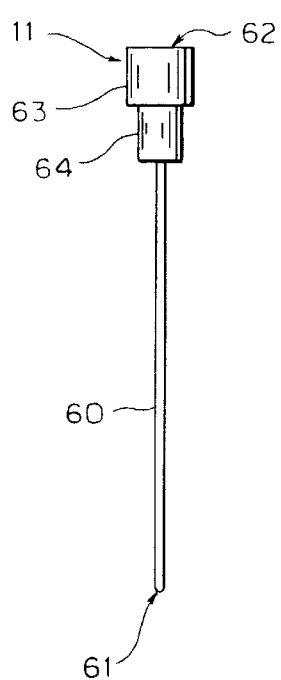
FIG. 2 is a front elevational view of the trocar of FIG. 1.

The enlarged opening 33 and conduit 40 are also formed to receive a trocar 11, as illustrated by FIG. 1. The trocar, shown separately in FIG. 2, comprises a pin 60 having a tip end 61 and a handle end 62. At the handle end 62, the trocar has a handle 63 which comprises an enlarged knob at the end of the pin 60 opposite the tip end 61. A stopper 64 is also provided between handle 63 and the pin 60. The stopper 64 preferably has a diameter slightly smaller than the handle 63. In embodiments of the delivery device having a connector 28 with an angled wall 36, the stopper 64 is sized to engage the angled wall 36 when the trocar 11 is inserted into the cannulated pin 10. Upon insertion of the trocar 11, the pin 60 fills the conduit 40 and extends to the pointed end 16 of the cannulated pin 10. The handle 63 may be grasped to withdraw the trocar 11 from the cannulated pin 10.

The trocar and cannulated pin are comprised of a biologically inert material, such as any metal customarily used for surgical devices and particularly those used for bone screws and pins. Materials such as titanium, stainless steel or other materials known in the surgical and medical arts may be used so long as they maintain their structural integrity notwithstanding the holes of the perforated portion. The connector 28 may comprise a rubber or other similar material.

The connector 28 and handle 63 of the delivery device 12 is engagable by a grip or other driving means for manually driving the device into the bone of a patient. In use, the device 12 is tapped into the bone of a patient so that the notch 21 penetrates the outer surface of the bone. The grip is then engaged to rotate the device 12 so that the device advances into the bone of the patient. The angled edges 22 and 23 cut through the bone while threads 50 advance the device into the bone. Because the delivery holes have a central axis angled in a direction toward the connection end 15 of the shaft 14, and away from the pointed end 16 of the shaft, bone fragments are not directed toward the delivery holes 41 as the device 21 advances into the bone. When the holes 41 are positioned within the patient's bone as desired, the grip is removed and the trocar 11 is withdrawn from the cannulated pin 10 by grasping the handle 63 and removing the trocar 11 from the conduit 40. Removing the trocar 11 leaves the conduit and delivery holes in communication with the bone of the patient. One of the standard I.V. tubes discussed above is then connected to the connector 28 of the cannulated pin 10. Fluids are introduced through the opening 33 and fed into the bone tissue of the patient via the delivery holes 41. The fluids which may be delivered via the cannulated pin include a number of fluids, such as water, and chemical and pharmaceutical agents, such as agents used in chemotherapy, antibiotics, bone morphogenic proteins ("BMPs"), bone growth factors, time released beads, and other fluids which are desirably introduced directly into bone.

Figure 7:
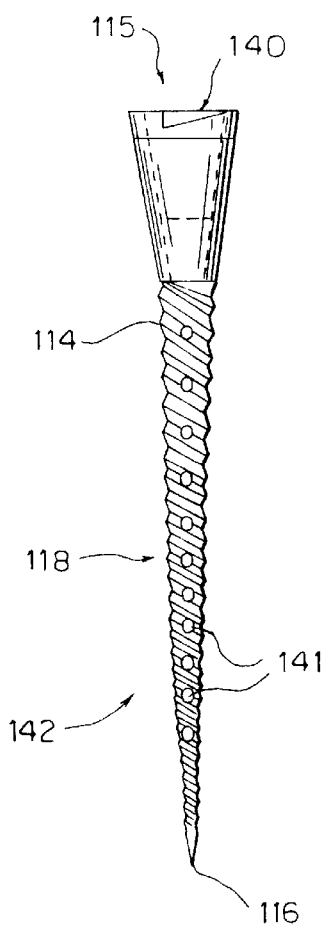
FIG. 7 is front elevational view of a cannulated pin in accordance with another embodiment of the invention.

An alternative embodiment for the cannulated pin is illustrated in FIG. 7. The cannulated pin has a threaded portion 118 extending from the pointed end 116 to the connection end 115. The perforated portion 142 having delivery holes 141 also extends substantially along the length of the shaft 114. The delivery holes 141 have a central axis angled toward the connection end 115 to prevent clogging of the delivery holes 141. The cannulated pin may also include a notch or other cutting edge at the pointed end 116 for tapping into the bone of the patient.

Figure 8:
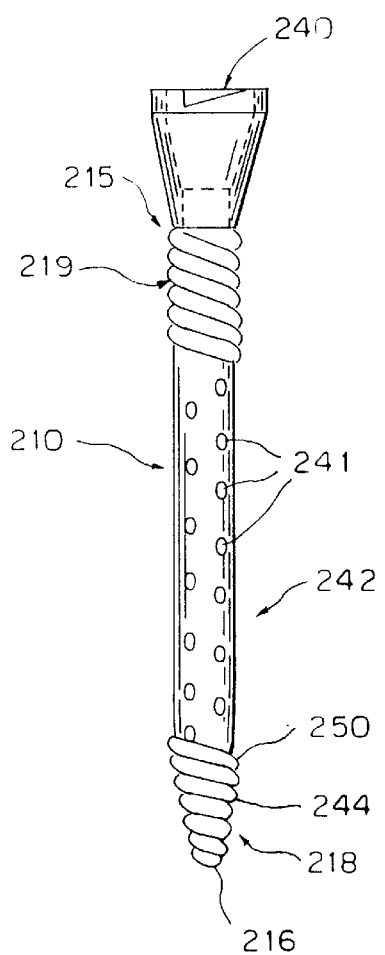
FIG. 8 is front elevational view of a cannulated pin in accordance with yet another embodiment of the invention.

Another embodiment is illustrated in FIG. 8, in which the cannulated pin includes interrupted threads so that the cannulated pin 210 includes a first threaded portion 218 adjacent the pointed end 216 of the cannulated pin 210, as well as a second threaded portion 219 adjacent the connection end 215. The delivery holes 241, in communication with conduit 240, are disposed on an unthreaded portion, also comprising perforated portion 242. Unlike the embodiment of FIGS. 1 through 6, the perforated portion 242 extends between the first threaded portion 218 and the second threaded portion 219 so that delivery holes 241 are not located on the curved segments 244 of the threads 250.

A cannulated pin in accordance with the invention may also be employed to fix another device to a bone. For instance, the cannulated pin may be used to fix to bone an external fixation device such as a distraction device for gradually enlarging the bone of a patient, or a reduction device for reducing the size of bone. A cannulated pin in accordance with the invention provides delivery holes, which are particularly desired for administering bone growth factors encouraging the formation of new bone growth.

Another aspect of the present invention is a method of installing a cannulated delivery pin to deliver fluids to the medullary cavity of a patient's bone. The method comprises inserting the delivery pin discussed above in connection with FIG. 8. The delivery pin is inserted by providing a cut in the cortical bone surrounding the medullary cavity, turning the delivery pin so that the threads bore through the cortical bone until the delivery holes on the non-threaded portion are disposed within the medullary cavity and both the first and second threaded portions are disposed within cortical bone surrounding the medullary cavity. Fluids are then introduced through the conduit and delivery holes into the medullary cavity. The cut may be provided by a self-tapping notch on the delivery pin or by a drill, as discussed above.

As will be readily appreciated, numerous other variations and combinations of the features discussed above will be employed without departing from the present invention. Accordingly, the foregoing description of certain preferred embodiments should be taken by way of illustration, rather than by way of limitation, of the features discussed above.

What is claimed is:

1. A delivery pin for administering fluids to the bone of a patient, comprising:
   a shaft having a connection end and a pointed end, a conduit being defined in the interior of the shaft, opening at the connection end of the shaft for communication of fluids into the shaft, and a plurality of delivery holes in the side walls of the shaft, communicating with said conduit; and
   a trocar having a pin with a tip at one end and a stopper at the other end, the pin of said trocar being sized so as to substantially fill the conduit of said shaft when inserted therein.

2. A delivery pin in accordance with claim 1, wherein said delivery holes each have a central axis tilted in a direction toward said connection end, such that the end of each hole facing the outside is closer to said connection end than the end facing the conduit.

3. A delivery pin in accordance with claim 1, wherein the pointed end of said shaft is closed and self-tapping.

4. The delivery pin of claim 1, wherein said shaft has at least a first threaded portion of said shaft, including threads for boring through bone, said threads being longitudinally spaced along said threaded portion.

5. The delivery pin of claim 4, wherein at least a portion of said plurality of delivery holes are disposed between said spaced threads and distributed on said threaded portion.

6. The delivery pin of claim 4, wherein said shaft includes a perforated portion and at least a portion of said plurality of delivery holes are disposed in said perforated portion.

7. The delivery pin of claim 6, wherein said first threaded portion comprises a portion of said shaft adjacent said pointed end.

8. The delivery pin of claim 7, wherein said first threaded portion extends from said pointed end to a first intermediate point comprising a second end of said first threaded portion, said second end being spaced from said connection end.

9. The delivery pin of claim 8, wherein said perforated portion extends from said second end of said first threaded portion to a location on said shaft adjacent said connection end.

10. The delivery pin of claim 8, wherein said perforated portion is unthreaded, and further comprising a second threaded portion extending from said connection end to a second intermediate point and said perforated portion extends from said second intermediate point to said first intermediate point of said first threaded portion so that said perforated portion extends between said second threaded portion and said first threaded portion.

11. The delivery pin of claim 5, further comprising curved segments of said shaft extending between said threads, said curved segments including surfaces facing said connection end and other surfaces facing said pointed end.

12. The delivery pin of claim 11, wherein said delivery holes communicate with said surfaces facing said connection end.

13. A method of administering fluids to a patient, comprising:

providing a delivery pin in accordance with claim 1;

inserting said trocar into the conduit of said shaft;

inserting said delivery pin into a bone;

removing said trocar from the conduit; and delivering fluids through said delivery holes.

14. A delivery pin for administering fluids to the bone of a patient, comprising a shaft having a connection end and a pointed end, a conduit being defined in the interior of the shaft, opening at the connection end of the shaft for communication of fluids into the shaft, and a plurality of delivery holes in the side walls of the shaft, communicating with said conduit, wherein said shaft includes a first externally threaded portion including threads longitudinally spaced along said threaded portion for boring through bone, segments of said shaft extending between such threads including surfaces facing said connection end and surfaces facing said pointed end, and wherein said delivery holes communicate with said surfaces facing said connection end.

15. A delivery pin in accordance with claim 14, further including a trocar having a pin with a tip at one end and a stopper at the other end, the pin of said trocar being sized so as to substantially fill the conduit of said shaft when inserted therein.

* * * * *